United States Patent [19]
Birks et al.

[11] 3,989,944
[45] Nov. 2, 1976

[54] PARALLEL-BEAM X-RAY OPTICS FOR MEASURING ASBESTOS

[75] Inventors: Laverne S. Birks, Potomac, Md.; Mohammad Fatemi, McLean, Va.

[73] Assignee: The United States of America as represented by the Secretary of the Navy, Washington, D.C.

[22] Filed: Sept. 5, 1975

[21] Appl. No.: 610,730

[52] U.S. Cl. ............................. 250/272; 250/273
[51] Int. Cl.² ........................................ G01N 23/20
[58] Field of Search .......... 250/272, 273, 274, 275, 250/277, 278, 279

[56] References Cited
UNITED STATES PATENTS

| | | | |
|---|---|---|---|
| 2,750,512 | 6/1956 | Meloy | 250/277 |
| 3,100,261 | 8/1963 | Bigelow | 250/272 |
| 3,309,518 | 3/1967 | Weiss | 250/273 |
| 3,596,092 | 7/1971 | Marjoram | 250/273 |
| 3,855,470 | 12/1974 | Sahores | 250/272 |

*Primary Examiner*—Craig E. Church
*Attorney, Agent, or Firm*—R. S. Sciascia; Philip Schneider; Melvin L. Crane

[57] ABSTRACT

A system for identifying chrysotile asbestos as well as other asbestiform fibers in air pollution samples which comprises a collimated x-ray beam which is incident on parallel aligned asbestos fibers. Diffracted x-rays are detected by a proportional counter set at the diffraction line position for the (002) plane. Background intensity may be detected by a second counter set above the axis, or the sample may be rotated 90° and the one detector used to detect diffracted and background x-rays.

7 Claims, 3 Drawing Figures

PARALLEL-BEAM X-RAY OPTICS FOR MEASURING ASBESTOS

CROSS REFERENCE TO RELATED APPLICATION

This application is related to application Ser. No. 610,728 and application Ser. No. 610,729 filed on even date.

BACKGROUND OF THE INVENTION

This invention relates to an x-ray analysis system and more particularly to x-ray optics for measuring asbestos within air samples.

Heretofore analysis of elements, samples of materials, crystals, etc., have been carried out by x-ray diffraction since it is well known that different material have characteristic x-ray patterns. Most fibers other than asbestos are single crystals with a major axis along the fiber direction. Preferred orientation is observed for planes normal to the fiber axis but not for planes parallel to the axis. Thus the measurement of asbestos fibers is very difficult especially in a mixed sample.

One factor which makes measurement of asbestos difficult is that the quantity which can be collected from a reasonable amount of air is far too small to measure with x-ray film cameras. Therefore diffractometers with electronic detectors are required, however other problems are introduced because of the peculiar morphology of crystalline matter. Chrysotile asbestos, like all crystals, has a characteristic x-ray diffraction pattern. However, platy serpentine has almost exactly the same x-ray pattern as chrysotile and many other clay minerals have very similar patterns. It has been determined that the morphology of chrysotile asbestos is like that of a "rolled up" sheet of crystalline matter with the $a$-axis parallel to the fiber axis, the $c$-axis is nearly perpendicular to the "tubular" wall, with the b-axis perpendicular to the a and c axis. Thus, the axes ($b$ and $c$) take different orientations depending on where on the fiber they are set up. Preferred orientation can be observed from the planes parallel to the fiber axis using the well-known techniques photographic, however such methods cannot be adapted to airborne asbestos samples since it is not possible to form the fibers in the required small oriented bundles. Further, it has been determined that even with an oriented sample in a standard diffractometer system the major crystal plane (002) diffracts equally well for all orientations. Therefore well known x-ray optics cannot be used for detecting asbestos in mixed samples. A suitable system has been set forth in a publication NRL Report 7874, QUANTITATIVE ANALYSIS OF AIRBORNE ASBESTOS BY X-RAY DIFFRACTION, by L. S. Birks, M. Fatemi, J. V. Gilfrich and E. T. Johnson, Naval Research Laboratory, Washington, D.C. 20375, which forms a part of this specification.

SUMMARY OF THE INVENTION

This invention is directed to a special x-ray diffraction geometry for distinguishing chrysotile asbestos as well as other asbestiform fibers from serpentine and other clay minerals. The x-ray method requires alignment of the asbestos fibers with a special detection technique for identifying the presence of asbestos in a sample. The system is suitable for detecting $0.2\mu g$ asbestos in the absence of extraneous material for real air samples.

DETAILED DESCRIPTION g asbestos

Figure 1:
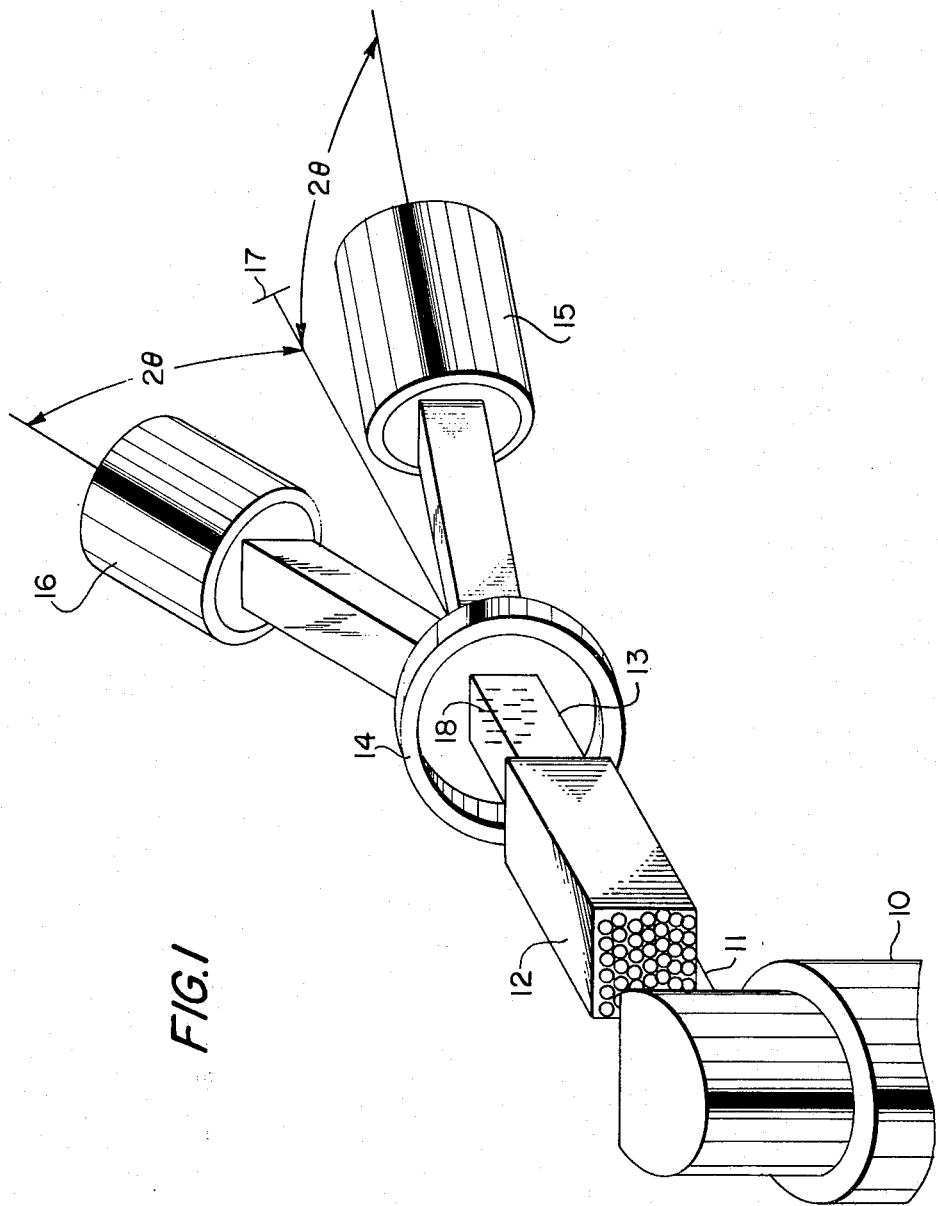
FIG. 1 illustrates an x-ray optic system made in accordance with this invention for quantitative measurement of aligned asbestos fibers.

Now referring to FIG. 1, there in shown by illustration an x-ray optic system made in accordance with the teaching of this invention. As shown the x-ray optic system includes a spectrograph type x-ray tube 10 which generates an x-ray beam 11 in the horizontal plane which has a large cross sectional beam area. The beam is directed into a tubular collimator 12 which collimates the x-ray beam into a broad beam of parallel rays 13. The collimated beam is directed onto an aligned asbestos sample 14 which is mounted with the fibers in a plane perpendicular to the x-ray beam and with the fibers aligned parallel to each other in the vertical plane. The x-ray beam is diffracted by the asbestos fibers into a normal mode detector 15 which measures the diffracted signal to the right of the normal beam, plus any scattering due to the substrate. A second detector 16 is positioned above the main beam in the parallel mode and measures scattering alone. The detector 16 is positioned at the same angle above the main beam as the detector 15 is placed to the right of the main beam. It has been determined that when using a chromium target x-ray tube the $2\theta$ diffraction from the (002) planes is about 18°. Therefore the two detectors will be placed at an angle of about 18° relative to the main beam. A beam stop 17 is provided to absorb the main beam to avoid harmful injury to personnel who may be otherwise affected. The detectors are adjustable on an arc in order to measure different diffraction angles $2\theta$.

The detectors 15 and 16 may be standard proportional counters set at the diffraction line position for the 002 plane.

In operation, asbestos fibers are aligned on a substrate and the substrate is oriented in the x-ray collimator system for maximum diffracted intensity when the fibers are parallel to the axis of the x-ray spectrometer. The x-rays are directed through the collimator onto the asbestos fiber-substrate. The x-rays are diffracted with scattered background onto the detector 15. Simultaneously, the scattered background is recorded by the detector 16. The difference in the two measurements is a measure of the asbestos in the sample.

The system has been shown with two detectors placed 90° apart where one detector detects diffracted x-rays along with background while the other detector detects background. The measurement could be carried out by use of a single detector by first positioning the detector in the position of detector 15 to detect diffracted x-rays and background then rotating the detector to the position of detector 16. Also, the detector could be left in the position of detector 15 and the sample may be rotated 90° normal with the beam so that the fibers are perpendicular to the spectrometer axis so that the signal and background maybe measured sequentially.

It has been determined that ordinary x-ray diffractometer optics cannot be used or modified to distinguish the chrysotile form even for aligned fibers because of the peculiar "rolled" nature of the abestos fibers.

In carrying out the method, the asbestos fibers are specifically orientated in substantially parallel alignment on a thin substrate with fibers spread over an area of about one centimeter. Therefore the x-ray beam should have a broad cross section.

U.S. Pat. No. 3,497,419 is directed to electrostatic alignment of asbestos fibers. This approach to alignment of asbestos fibers is not directly applicable to the present invention because the patent is concerned with long, silky industrial fibers and with large quantities of material. This invention is concerned with measurement of aerosol and other small samples to determine the presence and quantity of small asbestos elements in the sample.

In carrying out this invention to determine the unknown amount of asbestos in a sample, it was first necessary to prepare a sample with a known quantity of asbestos in order to provide a calibration standard. The following process was used to set up a pure asbestos calibration standard. Further, since the asbestos fibers are "silky" by nature, it has been determined that it is necessary to break the asbestos fibers down to fibril size to achieve best results.

The following method is carried out to break down the fibers to fibril size and to prepare a calibration sample.

About 4mg of UICC standard chrysotile asbestos fibers are placed in a wetting agent such as ½ ml of 1% Aerosol OT solution in water.

Figure 2:
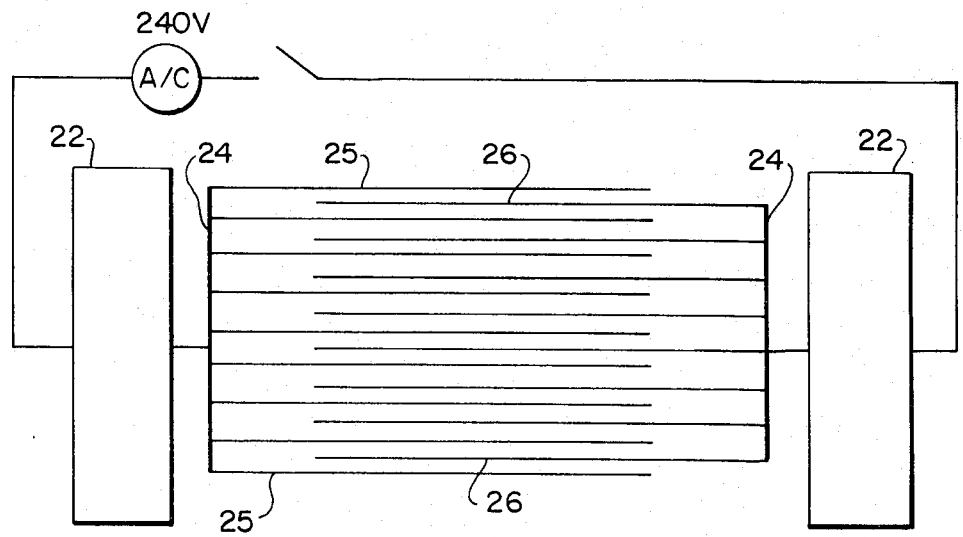
FIG. 2 illustrates a macrograph of an aligned asbestos sample.

Aerosol OT is a trade name of American Cynamid Co., which is dioctyl sodium sulfosuccinate. (The Aerosol OT is necessary as a dispersing agent). The suspension is sonicated for about 45 minutes at 100 watts power using a "cell disrupter", for reducing the size of the fibers to 1–4 $\mu$m long with a 0.1 $\mu$m diameter. A suitable "cell disrupter" is a model No. 16-850 manufactured by the Virtiz Co. The sonicated suspension is diluted with water to 500 ml making the asbestos concentration 6 $\mu$ g/ml. A 25 ml aliquot of the diluted suspension (150 $\mu$ g of asbestos) is vacuum filtered onto a 25 mm diameter disk 0.45 mm pore size of cellulous triacetate filter membrane such as (millipore HAWP, Gelman GA6). The disk of millipore is folded, placed into a test tube and ashed for about 2½ hours in a low-temperature radio-frequency asher such as a Perkin-Elmer No. Coleman 40. Subsequent to ashing 30 drops of 0.001% solution of parlodion (cellulose nitrate) in distilled amyl acetate is added to the ashed residue. The suspension is then sonicated for about 8 minutes to insure a homogeneous distribution of asbestos. One drop of the latter suspension containing 5$\mu$ g asbestos is placed onto a special electrode grid, FIG. 2, which includes conductors 22 which are connected to a power source 23. The conductors are connected to feeder electrodes 24 to which one end of grid electrodes 25, 26 are alternately connected. The power source 23 may be 240 bolts D.C. or A.C. The assembly is left undisturbed with the power applied until the droplet has completely dried. The power is then switched off and the electrodes are examined under an optical microscope for any unusual flaws in the sample. The electrodes are described in application Ser. No. 610,729.

Application of the power to the electrode of the grid causes the asbestos fibers to align themselves substantially parallel to each other and perpendicular to the grid wires. Therefore when the droplet has dried the asbestos fibers will remain aligned as set forth above.

A solution of 2.5% parlodion in amyl acetate is sprayed gently onto the dried sample to embed the fibers in a thin plastic film. The sprayed film is allowed to dry in a dust-free environment and subsequently stripped off the microelectrode assembly by dipping the grid into water in which the film with the aligned asbestos fibers attached floats to the surface of the water. The film is picked up by a ring-shaped lucite holder making sure that the film is wrinkle free and centrally aligned on the ring-shaped holder. The film is permitted to dry and is ready for measurement of the asbestos fibers. It has been determined that a thin film minimizes the background intensity contributed by x-ray scattering from the film during measurement.

The sample is then placed in the above described x-ray analyser and signal measurements are made which include signal and background as well as background. Samples containing different quantities of asbestos may be prepared and a calibration curve for the different quantities may be made.

Once the asbestos calibration standard has been made from known amounts of asbestos, analysis of actual particulate collections for asbestos content may be made. The unknown sample preparation is not completely the same as for the calibration samples because the unknown samples contain particulate matter other than asbestos. It has been determined that the sensitivity of the x-ray method is sufficient to give a limit of detection of 0.4 $\mu$ g for a 500 second counting time for samples containing extreneous matter.

In preparing samples containing pollutant asbestos, the pollutant sample contents are collected by use of membrane filters such as described above. The millipore filter containing the pollutant sample is placed in a test tube or other container and ashed for 2½ hours in a low temperature radio-frequency asher as set forth above.

The ashed sample is then dispersed in an aquous solution of Aerosol OT at moderate ultrasonic power (60 watts) for about 5 minutes. The total mass of particulate material is reduced by mild centrifugation (10 to 15 g's) for about 30 seconds to eliminate the largest particles. The supernatant suspension is then filtered to collect the asbestos and other fine particles, and washed with deionized water to remove soluble material. The filter and collected asbestos and particulate matter are ashed a second time in a low temperature RF reactor for about 3 hours. Subsequent to ashing the second time, the steps as set forth above for the calibration sample are followed. That is those steps subsequent to ashing the millipore filter starting with adding 30 drops of a 0.001% solution of paralodion in distilled amyl acetate to the ashed residue and sonication thereof. The output signal obtained by the x-ray system is compared with the calibration curve to determine the presence and quantity of asbestos in the obtained sample.

Figure 3:
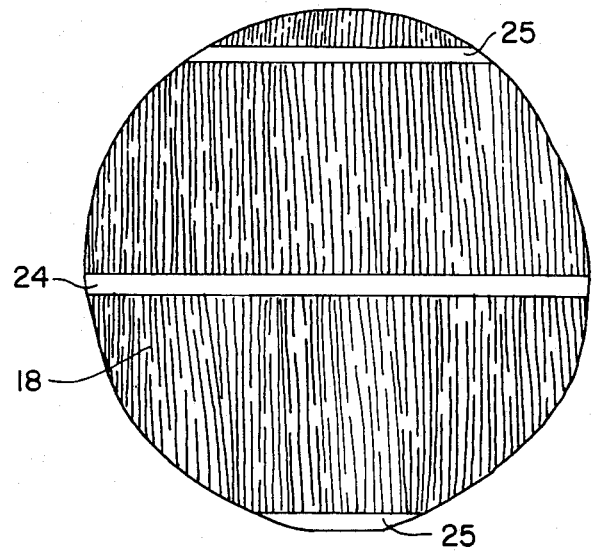
FIG. 3 illustrates a special multi-electrode grid used in the alignment of asbestos fibers.

Preparation of the specimen which includes the asbestos particulate matter for use in the x-ray system is carried out by use of the special multi-electrode grid as shown in FIG. 3, wherein the electrodes are interdigitaled chromium lines 50 $\mu$m wide by 1200 A thickness and separated by about 1 mm.

The micro-electrode assembly is formed in accordance with procedures which are well known in micro-electronics such as the following:

1. A "master" is prepared 10 times as large as the desired product and photoreduced on a quartz flat.
2. Quartz discs with a 1200-A layer of evaporated chromium are obtained either commercially or from a vacuum evaporation facility. Quartz is desirable because it cleans better than glass and vacuum deposition is more suitable than sputtering due to its more gentle treatment.
3. The chromium plated side of the discs are sprayed with photoresist and baked at 300° F for about 15 minutes.
4. The original is placed in contact with the photoresist and exposed to ultraviolet light for about 10 minutes.
5. The exposed disk is "developed" to remove the unexposed photoresist.
6. The exposed chromium is etched away.
7. The photoresist is dissolved and the grid is washed, dried, and inspected for continuity.

FIG. 3 illustrates the asbestos particles aligned by the electrode grid. The view in an enlarged section which illustrates only a portion of three parallel electrodes with the fibers aligned therebetween.

The above described method of distinguishing chrysotile asbestos by use of broad beam optics in combination with sample rotation in a plane normal to the x-ray beam, by detection with two detectors 90° apart off the axis, or by using one detector and rotating the detector 90° is the only known methods of distinguishing chrysotile asbestos from other forms of asbestos, by x-ray diffraction technique.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of The United States is:

1. A system for identifying and determining the amount of asbestos fibers in a prepared sample which comprises:
   an x-ray tube for generating a desired beam of x-rays;
   a collimator for collimating said x-rays into a broad beam;
   a sample holder for holding said prepared sample of asbestos fibers in the path of said broad beam of x-rays with said asbestos fibers aligned perpendicular to the axis of said collimated x-ray beam;
   an x-ray diffraction detector positioned off the axis of said collimated x-ray beam at the diffraction line position for the (002) plane to measure the diffraction signal plus background signal; and
   means for rotating said detector 90° on an arc in a plane perpendicular to the axis of said collimated x-ray beam to measure the background signal,
   whereby the difference between said detected diffraction signal plus background signal and said background signal is a measure of asbestos fibers in said sample.

2. A system for identifying and determining the amount of asbestos fibers in a prepared sample which comprises:
   an x-ray tube for generating a desired beam of x-rays;
   a collimator for collimating said x-ray beam into a broad beam;
   a sample holder for holding said prepared sample of asbestos fibers in the path of said collimated broad beam of x-rays with said asbestos fibers aligned in a plane perpendicular to the axis of said collimated x-ray beam;
   a first x-ray diffraction detector positioned off the axis of said collimated x-ray beam at the diffraction line position for the (002) plane to measure the diffraction signal plus background signal; and
   a second x-ray diffraction detector positioned 90° on an arc from said first detector on the same plane which plane is perpendicular to said collimated x-ray beam to detect only background signals with both detectors positioned off the axis of said collimated x-ray beam at equal angles relative to the axis of said collimated x-ray beam,
   whereby the difference between said detected diffraction signal plus background signal and said detected background signal is a measure of asbestos fibers in said sample.

3. A system as claimed in claim 2 which includes:
   means for rotating each of said detectors relative to the x-ray beam axis on separate arcs in planes paralleling the axis of said collimated x-ray beam to measure different diffraction angle signals.

4. A system for identifying and determining the amount of asbestos fibers in a prepared sample which comprises:
   an x-ray tube for generating a desired beam of x-rays;
   a collimator for collimating said x-rays into a broad beam;
   a rotatable sample holder rotatable in a plane perpendicular to the axis of said collimated beam for holding said prepared sample in the path of said broad beam of x-rays with said asbestos fibers aligned in a plane perpendicular with the axis of said collimated x-ray beam through a rotation of 90°;
   one x-ray diffraction signal detector positioned off the axis of said collimated x-ray beam to detect a diffracted signal plus background signals; and
   means for rotating said sample holder and said sample an angle of 90° about the axis of said collimated x-ray beam to position the linear axis of said asbestos fibers at a different angle relative to said collimated x-ray beam so that said detector detects only a background signal;
   whereby the difference between said detected diffraction signal plus background signal and said background signal is a measure of asbestos fibers in said sample.

5. A method of identifying and determining the amount of asbestos in a prepared sample; which comprises
   aligning said particles in parallel relationship to each other,
   placing said sample in an x-ray excitation system with said parallel aligned particles in the vertical plane and perpendicular to the horizontal plane for receiving incident x-rays,
   positioning a pair of detectors 90° with respect to each other with one detector on the horizontal plane and the other detector in the vertical plane with the detectors on equal arcs from the normal x-ray beam axis,
   whereby one detector detects diffracted and background x-rays and the other detector detects background x-rays, and determining the difference between the two detected outputs to determine the amount of asbestos in said sample.

6. A method of identifying and determining the amount of asbestos in a prepared sample which comprises:
aligning said asbestos particles parallel with each other in a fixed sample,
placing said sample to be identified into an x-ray excitation system with said particles in the verticle plane for receiving incident collimated x-rays,
positioning a detector off the axis of said incident x-ray path for detecting diffracted and background x-rays from said sample,
rotating the sample 90° in the vertical plane, and
detecting background radiation with said detector determining the difference in the detected output at each position which is a measure of the asbestos present.

7. A method of identifying and determining the amount of asbestos in a prepared sample; which comprises
aligning said asbestos particles parallel with each other in a fixed sample,
placing said sample in an x-ray excitation system with said aligned particles in the vertical plane perpendicular to the horizontal for receiving incident x-rays,
positioning a detector off the axis of said incident x-ray path for detecting diffracted characteristic x-rays and background x-rays,
rotating said detector 90° in an arc of equal radii to detect background radiation,
determining the difference between the two detected outputs to determine the amount of asbestos in said sample.

* * * * *